United States Patent
Lindquist et al.

[11] Patent Number: 5,990,375
[45] Date of Patent: Nov. 23, 1999

[54] SHEATING LAMINATE FOR AN ABSORBENT PRODUCT, PROCESS FOR MANUFACTURE OF THE SHEATHING LAMINATE AND ABSORBENT PRODUCT CONTAINING SUCH SHEATHING LAMINATE

[75] Inventors: Bengt Lindquist, Lerum; Thomas Böhm, Västra Frölunda, both of Sweden

[73] Assignee: SCA Hygiene Products Aktiebolag

[21] Appl. No.: 08/916,294

[22] Filed: Aug. 22, 1997

Related U.S. Application Data

[63] Continuation of application No. 08/619,505, Jun. 18, 1996, abandoned.

[30] Foreign Application Priority Data

Oct. 15, 1993 [SE] Sweden .................................. 9303406

[51] Int. Cl.[6] ............................ A61F 13/15; A61F 13/20
[52] U.S. Cl. ........................................... 604/378; 604/383
[58] Field of Search ................................. 604/378, 383, 604/385.1, 385.2; 156/324.4, 306.6, 554, 303, 324, 244.11, 244.12, 244.27

[56] References Cited

U.S. PATENT DOCUMENTS

| | | | |
|---|---|---|---|
| 4,330,353 | 5/1982 | Kunimoto et al. | 156/324.4 |
| 4,420,353 | 12/1983 | Levine | 156/324.4 |
| 4,515,649 | 5/1985 | Nussabaum | 156/306.6 |
| 4,637,949 | 1/1987 | Manning et al. | 156/306.6 |
| 4,731,276 | 3/1988 | Manning et al. | 156/306.6 |
| 5,304,161 | 4/1994 | Noel et al. | 604/378 |
| 5,370,764 | 12/1994 | Alikhan | 156/324 |
| 5,415,640 | 5/1995 | Kirby et al. | 604/383 |
| 5,447,507 | 9/1995 | Yamamoto | 604/387 |
| 5,472,437 | 12/1995 | Akyama et al. | 604/387 |

FOREIGN PATENT DOCUMENTS

WO 93/09744 5/1993 WIPO.
WO 93/12745 7/1993 WIPO.

*Primary Examiner*—John G. Weiss
*Assistant Examiner*—Ki Yong
*Attorney, Agent, or Firm*—Burns, Doane, Swecker & Mathis LLP

[57] ABSTRACT

The invention relates to a sheathing laminate for an absorbent product, such as a sanitary napkin, a diaper, an incontinence protector or the like, and which is to be used as a liquid permeable top layer, which, when the product is in use, faces the body of the user. The laminate (30) comprises a web (10) of plastic film, to one side of which are fixed two mutually spaced, longitudinal strips (14, 16) of non-woven material, while to the other side of the plastic film web (10)—in an area between the two strips (14, 16) on the opposite side of the plastic film web—there is fixed a longitudinal intermediate strip (26) of non-woven material. When used on an absorbent product, the laminate has perforations (42) at least within a portion of the area of the intermediate non-woven strip (26). The invention also relates to a process for manufacture of the sheathing laminate.

17 Claims, 3 Drawing Sheets

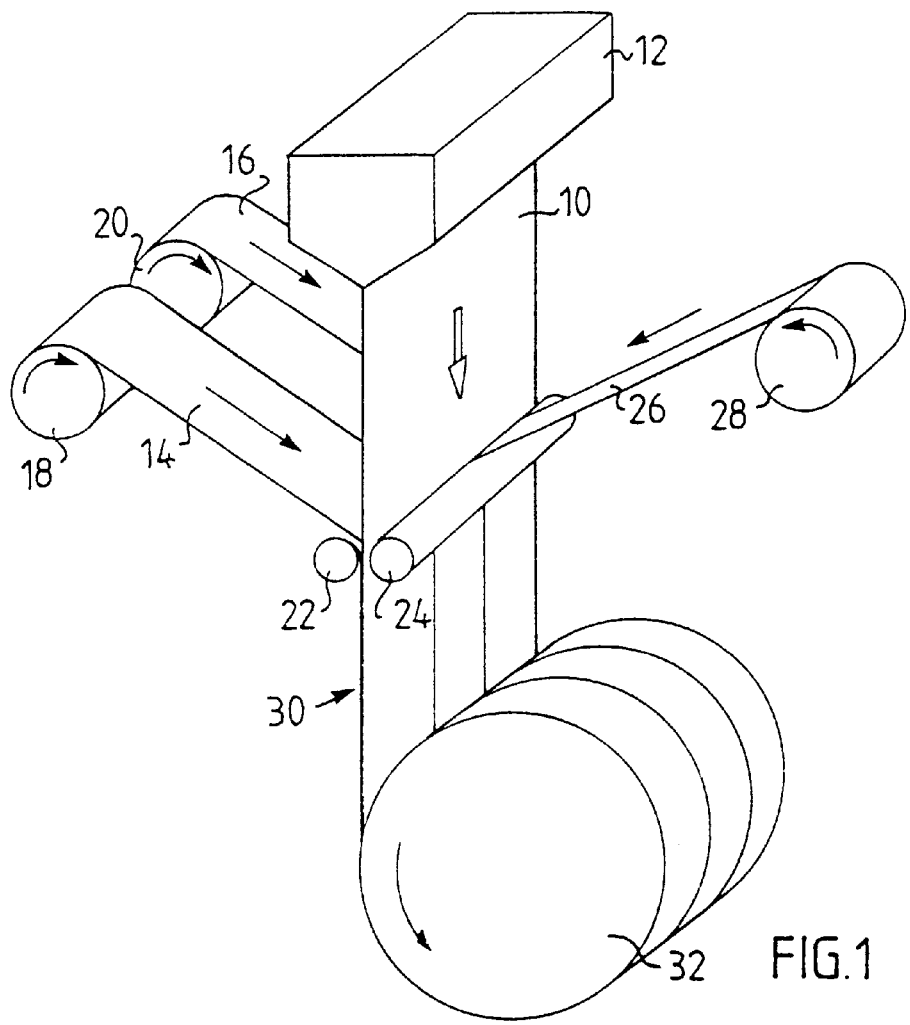
FIG. 1
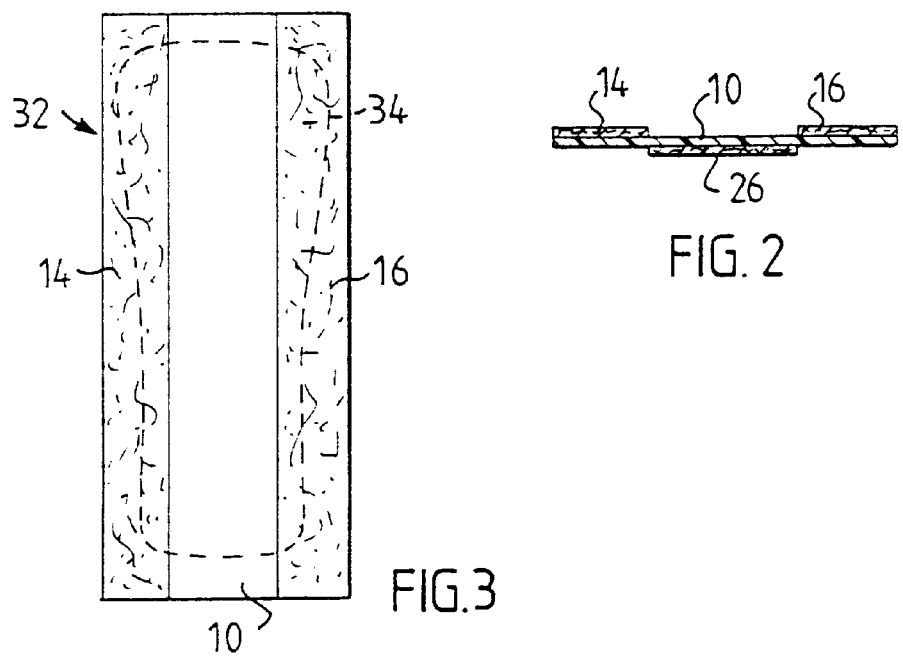
FIG. 2
FIG. 3

SHEATING LAMINATE FOR AN ABSORBENT PRODUCT, PROCESS FOR MANUFACTURE OF THE SHEATHING LAMINATE AND ABSORBENT PRODUCT CONTAINING SUCH SHEATHING LAMINATE

This application is a continuation of application Ser. No. 08/619,505, filed Jun. 18, 1996 now abandoned.

The present invention relates to a sheathing laminate for an absorbent product, such as a sanitary napkin, a diaper, an incontinence protector or the like.

In absorbent products of the above-mentioned type, it is known to use as a fluid permeable outer layer, which during use is intended to face the user, a plastic net or a perforated plastic film. Such surface materials have good rewetting properties, so that the absorbent body when used is felt to have a dry and comfortable surface. A disadvantage is, however, that the edges of the net or plastic film can chafe and be felt to be sharp against the skin of the user.

To avoid this disadvantage, it has previously been suggested (see SE-A-9103853-9) that the edges of the net or plastic film be covered will a fold of soft, skin-friendly material, preferably a non-woven material. Making such folds presents, however, certain difficulties as does fixing the same to the net or the perforated plastic film at high production speed. Furthermore, a sheathing layer constructed in this manner cannot be prepared ahead of time and stored intermediately in a roll.

In order to eliminate the above-mentioned difficulties of the known technology in the field, it is suggested according to the present invention that the laminate comprises a web of plastic film to a first side of which, being that side which is intended to face the user's body, there are fixed two spaced, longitudinal strips of non-woven material, while to the other second side of the plastic web—in an area between the two strips on said first side of the plastic film web—there is fixed a longitudinal intermediate strip of non-woven material. This provides a surface material which has soft textile lateral edge portions which do not need to be folded over edge portions of the net or the perforated plastic film and which during manufacture can be rolled up into a roll for intermediate storage prior to manufacture of the absorbent products themselves.

In order to facilitate rolling up into an essentially homogeneous roller, the intermediate strip has a width corresponding to the space between the spaced strips at the same time as all of the strips have preferably the same thickness.

In a preferred embodiment of the sheathing laminate according to the invention, the spaced strips extend along the lateral edges of the plastic film web and can be joined by glueing, welding, heat calendering or the like to the lateral edges of a fluid impermeable sheathing layer forming the outer side, i.e. the side of the absorbent product facing away from the user.

According to an additional embodiment of the present invention, at least one of the separate spaced strips is located spaced inside the adjacent lateral edge of the plastic film web, thus forming the free lateral edge zone of the plastic film web which is unperforated. Thus, the sheathing laminate can completely envelope an absorbent body and form the fluid impermeable sheathing layer which faces away from the user. Alternatively, the width of said strips spaced from each other can be substantially greater than the width of the intermediate strip, and the sheathing laminate can in this case as well completely envelope the absorbent body, but in this case provide a soft textile surface on the outside of the final product as well.

The intermediate strip, which is intended to be disposed on the side of the plastic film web which faces away from the user, has good fluid conducting properties in order to divert liquid to an adjacent absorbent body of the final product.

In order to make the sheathing laminate fluid permeable when used as a top layer on an absorbent product, the laminate has perforations at least within a portion of the area of the intermediate strip. These perforations can have varied shape and/or size in a manner suitable for the purpose.

The invention also relates to a process for manufacture of a sheathing laminate for absorbent products, such as sanitary napkins, diapers, incontinence protectors and the like, which process is characterized in that at least one pair but preferably a plurality of pairs of mutually spaced, longitudinal strips of non-woven material are moved towards and fixed to one side of a plastic film web, that an additional longitudinal intermediate strip of non-woven material is fixed to the other side of the plastic film web on portions thereof which lie between respective pairs of the mutually spaced strips on the opposite side.

It is suitable that at least one of the strips of non-woven material be moved towards and fixed to the plastic film web in semi-molten state. Alternatively, the strip can be fixed to various places along the plastic film web and with other adhesive methods, such as glueing, heat calendering, ultrasonic welding or the like.

In order to make the sheathing laminate liquid permeable when used as a top layer on an absorbent product, the sheathing laminate is perforated at least within a portion of the area for each intermediate strip.

Finally, the invention emcompasses an absorbent product, such as a sanitary napkin, a diaper, an incontinence protector or the like, which comprises an absorbent body enveloped between a liquid impermeable bottom layer and a liquid permeable top layer, which when the product is used faces the body of the user, whereby according to the invention the top layer is a laminate, comprising a longitudinal plastic film piece, to a first side of which, being that side which is intended to face the user's body, there are fixed two mutually spaced longitudinal strips of non-woven material, extending over at least the lateral edge portion of the product, while to the other second side of the plastic film piece there is fixed an additional longitudinal strip of non-woven material in the liquid absorbing area between the two steps on said first opposite side of the plastic film piece, said laminate having perforations at least within a portion of the area for the intermediate non-woven strip.

Additional features and advantages of the present invention will be revealed in more detail below with reference to the accompanying drawings, of which:

FIG. 1 shows schematically the principle for manufacturing a sheathing laminate according to the invention;

FIG. 2 shows a cross-section through the laminate web made in FIG. 1;

FIG. 3 shows a plan view of a sheathing laminate piece with indicated placement of the absorbent body;

FIG. 1 shows schematically the principle of manufacturing a laminate web from which there are to be made individual fluid permeable sheathing layers for fluid absorbent products, such as sanitary napkins, diapers, incontinence protectors and the like.

Figure 4:
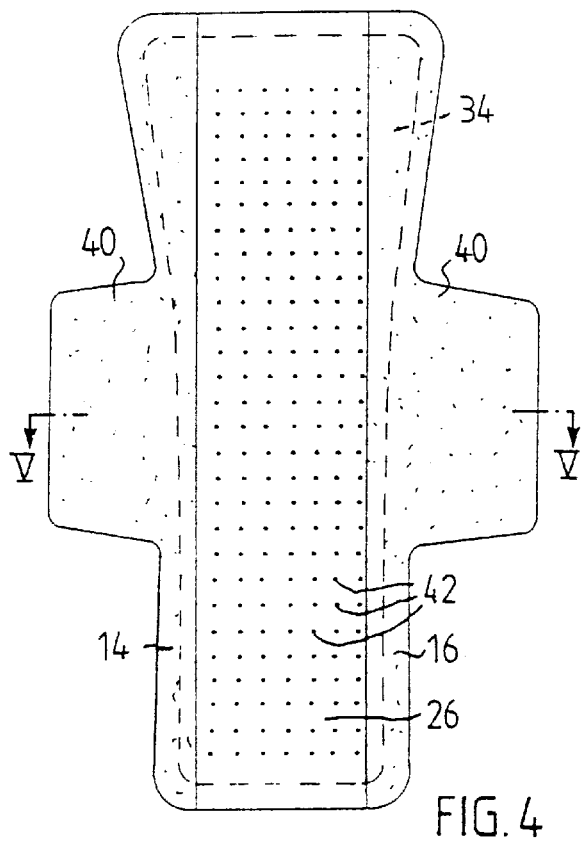
FIG. 4 shows an embodiment of an absorbent product with a sheath laminate according to the invention and with attachment tabs integrated with the laminate.

A plastic film web 10 is formed by an extrusion die 12 and moves vertically downwards. The plastic film web 10 is laminated on its one side with two mutually spaced strips 14 and 16 of non-woven material suitable for the purpose. In the example shown, these strips are unwound from respective storage rolls 18 and 20 and are fixed to the edge portions of the plastic film web 10 which is in a semi-molten state, with the aid of press rollers 22 and 24, while the other side of the plastic film web 10 is laminated at the same time with a third strip 26 of non-woven material, which is wound off from a roll 28, the width of said third strip essentially corresponding to the distance between the strips 14 and 16. The sheathing laminate web 30 thus formed is wound unto a roll 32 and can be intermediately stored thereon, before the web 30 in the subsequent manufacture of individual absorbent products, is cut into separate sheathing layers, which are to form the top layer, i.e. the side facing the user, of the final product.

The mutually spaced strips 14, 16 of non-woven material are intended to form comfortably soft, skin-contacting textile edge portions of the final product.

The non-woven strip 26 should, however, have the property of being able to conduct fluid from the wearer of the absorbent product to an absorbent body lying inside, and be able to visually mask the absorbed fluid. At the same time, the intermediate strip 26 serves as a spacing layer between the user and the fluid which has been absorbed into the absorbent body lying inside the product.

Suitable materials for use in the non-woven strips 14, 16 and 26 are, for example, fibres of synthetic polymers, such as polypropylene, polyester and polyethylene, individually or in the form of mixtures, co-polymers or bi-component fibres. Non-woven materials including cellulose based fibres such as rayon, cotton, cellulose fluff or the like, can also be used. The non-woven material can also be made by any known method which is suitable for the purpose.

It is suitable that the strips 14, 16 and 26 have essentially the same thickness, which facilitates winding up of the laminate web 30 into a roll 32 for intermediate storage.

In order to make the sheathing laminate permeable to fluid when used as a top layer in an absorbent product, the laminate is provided with a perforation at least within the area of the central portion of the absorbent product, preferably within the area coinciding with the intermediate non-woven strip 26 lying along the central portion. The perforations can have varying shape and size within various areas of the sheathing laminate. The perforation can also be of the type described in SE-C-8402614-5, and can be made either after the lamination but prior to rolling up of the roll 32, or in connection with the manufacture of the final product, i.e. the absorbent product.

Despite the fact that FIG. 1 shows the manufacture of a single sheathing laminate web 30, it is possible within the scope of the invention and suitable to simultaneously manufacture a number of sheathing laminate webs 30 in parallel, i.e. on a common width of plastic film web to laminate a plurality of pairwise mutually spaced non-woven strips 14, 16, on one side of the web and intermediate strips 26 at intended locations on the other side. Such a broad multiple web can then be cut longitudinally into a plurality of separate laminate webs 30, either prior to winding up into rolls 32 or at the subsequent manufacture of the final product, which can be done in direct connection with the manufacture of the laminate in a so-called in-line-production.

FIG. 3 shows a plan view of a piece of sheathing laminate 32 cut out of the laminate web 30, where the placement of the underlying absorbent body 34 is indicated.

Figure 5:
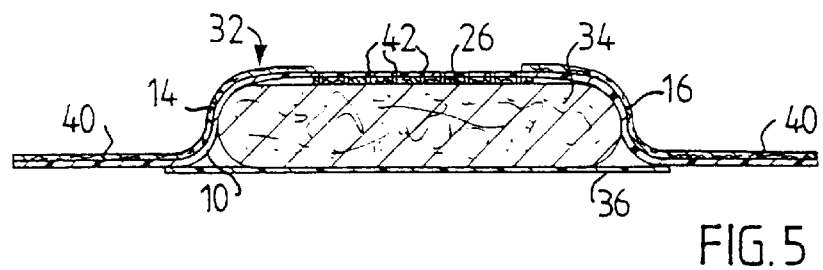
FIG. 5 shows a cross-section taken along the line V—V in FIG. 4.

FIGS. 4 and 5 show in more detail an embodiment of an absorbent body (sanitary napkin) with a fluid permeable sheathing laminate according to the invention as a top layer, i.e. the sheathing layer of the product lying closest to the body. The sanitary napkin comprises a conventional longitudinal absorbent body 34 preferably of fluff pulp with or without mixed-in so-called super-absorbents, which are enclosed between a liquid impermeable bottom layer 36 of suitable plastic material and a fluid permeable top layer of the sheathing laminate 32 according to the present invention. Other known materials for the absorbent body and the bottom layer can of course be used within the scope of the invention. The top layer is thus made of a plastic film 10 with a central strip 26 of non-woven material placed between the plastic film 10 and the absorbent body 34, and two lateral strips 14, 16 of non-woven material applied on the outside of the plastic film 10 at the edge portions of the napkin. The plastic film 10 is joined in a suitable manner to the bottom layer 36, for example by glueing or ultrasonic welding. The lateral strips 14, 16 can be made with attachment tabs or wings 40 extending laterally to facilitate fixing of the sanitary napkin in the crotch of a pair of underpants. The wings 40 can thus be formed in one piece with the strip 14, 16, or separate wings can be joined in a suitable manner to the strips 14, 16 or with the plastic film 10 or the bottom layer 36.

At least in the fluid absorbing zone of the sanitary napkin, i.e. the area of the intermediate strip 26, perforations 42 of suitable shape and distribution are made through the plastic film web 10 and the strip 26 to conduct bodily fluid into the absorbent body 34 of the sanitary napkin.

Figure 6:
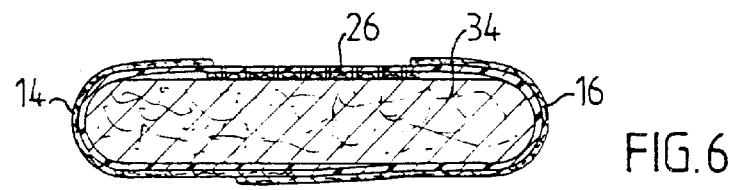
FIG. 6 shows a cross-section through an alternative embodiment of an absorbent product according to the invention.
Figure 7:
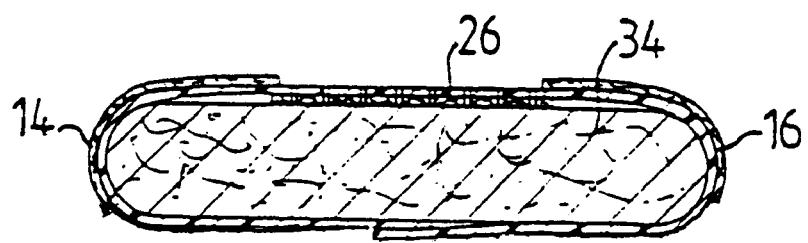

FIG. 6 shows an additional embodiment of an absorbent body with a sheathing laminate according to the present invention. In this embodiment, the plastic film 10 and the lateral strips 14, 16 have been made so wide that the laminate sheathing itself can envelop the entire absorbent body 34. Alternatively, the lateral strips 14, 16 of non-woven material can be made less broad, so that only the plastic film 10 can form the fluid impermeable bottom layer of the product, as shown in FIG. 7. One or both of the lateral strips 14, 16 may be spaced inside of the respective lateral edges of the plastic film 10.

We claim:

1. A sheathing laminate for an absorbent product, such as a sanitary napkin, a diaper and an incontinence protector, comprising:
   a web of plastic film having a first side and a second side opposing said first side;
   two mutually spaced, longitudinal strips of nonwoven material directly attached to said first side; and
   a longitudinal intermediate strip of nonwoven material having a width which does not exceed a distance between said mutually spaced longitudinal strips directly attached to said second side in an area between said two strips on said first side of the plastic film web.

2. Sheathing laminate according to claim 1, wherein the intermediate strip has a width which is essentially the same as the distance between the two mutually spaced strips.

3. Sheathing laminate according to claim 1, wherein the two mutually spaced strips extend along lateral sides of the plastic film web.

4. Sheathing laminate according to claim 1, wherein at least one of the two mutually spaced strips is spaced inside a respective lateral edge of the plastic film web.

5. Sheathing laminate according to claim 1, wherein the two mutually spaced strips and the intermediate strip of nonwoven material have essentially a same thickness.

6. Sheathing laminate according to claim 1, wherein a width of said mutually spaced strips is substantially greater than the width of the intermediate strip.

7. Sheathing laminate according to claim 1, wherein the two mutually spaced strips of nonwoven material have super-absorbent, gel-forming properties.

8. Sheathing laminate according to claim 1, wherein the intermediate nonwoven strip has fluid conducting properties.

9. Sheathing laminate according to claim 1, wherein the web of plastic film has perforations at least within a portion of the area to which the intermediate strip is fixed.

10. Sheathing laminate according to claim 1, wherein at least a portion of said intermediate strip is liquid pervious.

11. An absorbent product, such as a sanitary napkin, a diaper, and an incontinence protector, including the sheathing laminate according to claim 1, said absorbent product further comprising:
    an absorbent body enclosed between a fluid impermeable bottom layer and a fluid permeable top layer which during use of the product faces a user's body,
        wherein the top layer comprises the sheathing laminate, and
    wherein said sheathing laminate further includes perforations at least within a portion of the area for the intermediate nonwoven strip.

12. Product according to claim 11, wherein the intermediate nonwoven strip disposed on the inside of the plastic film piece has fluid conducting properties.

13. Product according to claim 11, wherein two longitudinal, opposite lateral edges of the product each have a laterally projecting fixing tab integrated with the sheathing laminate.

14. An absorbent product according to claim 11, wherein the sheathing laminate is liquid pervious.

15. A process for the manufacture of a sheathing laminate for absorbent products, such as sanitary napkins, diapers, and incontinence protectors, comprising the steps of:
    forming a semi-molten plastic film web by die extrusion, said plastic film web having a first surface and a second surface;
    directing at least one pair of mutually spaced, longitudinal strips of nonwoven material to spaced positions on said first surface of said semi-molten plastic film web;
    directing an additional longitudinal intermediate strip of nonwoven material to said second surface of said semi-molten plastic film web to a portion thereof which lies between said spaced positions to which the longitudinal strips of nonwoven material which are directed on said first surface of said plastic film web;
    directly attaching said nonwoven strips to said semi-molten plastic web with the aid of press rollers; and
    lowering the temperature of said laminate comprising said plastic film web and said strips of nonwoven material in order to solidify said plastic web and consolidate bonds between said plastic film web and said nonwoven strips.

16. Process according to claim 15, wherein the sheathing laminate formed is intermediately stored by rolling up prior to manufacture of the absorbent products.

17. Process according to claim 15, wherein the sheathing laminate is perforated at least within a portion of the area for each intermediate strip.

* * * * *